(12) United States Patent
Stelzer et al.

(10) Patent No.: US 9,857,577 B2
(45) Date of Patent: Jan. 2, 2018

(54) MICROSCOPE WITH A VIEWING DIRECTION PERPENDICULAR TO THE ILLUMINATION DIRECTION

(71) Applicant: European Molecular Biology Laboratory (EMBL), Heidelberg (DE)

(72) Inventors: Ernst H. K. Stelzer, Meckesheim (DE); Sebastian Enders, Stuttgart (DE); Jan Huisken, San Francisco, CA (US); Steffen Lindek, Plankstadt (DE); James H. Swoger, Barcelona (ES)

(73) Assignee: European Molecular Biology Laboratory (EMBL), Heidelberg (DE)

( * ) Notice: Subject to any disclaimer, the term of this patent is extended or adjusted under 35 U.S.C. 154(b) by 334 days.

(21) Appl. No.: 13/746,597

(22) Filed: Jan. 22, 2013

(65) Prior Publication Data

US 2014/0042339 A1 Feb. 13, 2014

Related U.S. Application Data

(60) Continuation of application No. 12/468,517, filed on May 19, 2009, now abandoned, which is a division of
(Continued)

(30) Foreign Application Priority Data

Dec. 9, 2002 (DE) .................................. 102 57 423

(51) Int. Cl.
*G02B 21/06* (2006.01)
*G02B 21/00* (2006.01)
(Continued)

(52) U.S. Cl.
CPC ..... *G02B 21/0032* (2013.01); *G01N 21/4795* (2013.01); *G01N 21/6458* (2013.01);
(Continued)

(58) Field of Classification Search
None
See application file for complete search history.

(56) References Cited

U.S. PATENT DOCUMENTS 4,035,535 A 7/1977 Taylor
4,621,911 A * 11/1986 Lanni .................... G02B 21/16
359/386
(Continued)

FOREIGN PATENT DOCUMENTS

DE 4326473 A1 2/1995
DE 19720513 A1 11/1998
(Continued)

OTHER PUBLICATIONS

European Office Action, dated Mar. 12, 2010, with translation.
(Continued)

*Primary Examiner* — Arnel C Lavarias
(74) *Attorney, Agent, or Firm* — Rothwell, Figg, Ernst & Manbeck, p.c.

(57) ABSTRACT

A microscope and imaging method in which a layer of the sample is illuminated by a thin strip of light and the sample is viewed perpendicular to the plane of the strip of light. The depth of the strip of light thus essentially determines the depth of focus of the system. To record the image, the object is displaced through the strip of light, which remains fixed in relation to the detector, and fluorescent and/or diffused light is captured by a planar detector. Objects that absorb or diffuse a large amount of light are viewed from several spatial directions. The three-dimensional images, which are captured from each direction can be combined retrospectively to form one image, in which the data is weighted according to its resolution. The resolution of the combined image is then dominated by the lateral resolution of the individual images.

34 Claims, 4 Drawing Sheets

US 9,857,577 B2

Page 2

Related U.S. Application Data application No. 10/538,081, filed as application No. PCT/EP03/05991 on Jun. 6, 2003, now Pat. No. 7,554,725.

(51) Int. Cl.
  G01N 21/64    (2006.01)
  G01N 21/47    (2006.01)
  G02B 21/16    (2006.01)
  G02B 21/36    (2006.01)
  G02B 21/26    (2006.01)

(52) U.S. Cl.
  CPC ..... *G02B 21/0048* (2013.01); *G02B 21/0056* (2013.01); *G02B 21/0076* (2013.01); *G02B 21/06* (2013.01); *G02B 21/16* (2013.01); *G02B 21/26* (2013.01); *G02B 21/367* (2013.01)

(56) References Cited

U.S. PATENT DOCUMENTS

| | | | |
|---|---|---|---|
| 4,700,298 A | 10/1987 | Palcic et al. | |
| 4,746,800 A | 5/1988 | Van Eijk et al. | |
| 4,850,779 A | 7/1989 | Cashell et al. | |
| 4,852,985 A | 8/1989 | Fujihara et al. | |
| 4,893,008 A | 1/1990 | Horikawa | |
| 5,104,218 A | 4/1992 | Garner | |
| 5,570,228 A | 10/1996 | Greenberg | |
| 5,710,625 A | 1/1998 | Neumann et al. | |
| 5,903,781 A | 5/1999 | Huber | |
| 6,249,341 B1 | 6/2001 | Basiji et al. | |
| 6,294,327 B1 | 9/2001 | Walton et al. | |
| 7,218,393 B2 | 5/2007 | Sharpe et al. | |
| 7,554,725 B2* | 6/2009 | Stelzer | G02B 21/06 359/385 |
| 8,711,211 B2 | 4/2014 | Betzig | |
| 8,970,950 B2* | 3/2015 | Stelzer | G02B 21/06 359/385 |
| 9,645,378 B2* | 5/2017 | Hilbert | G02B 21/06 |
| 2002/0163717 A1 | 11/2002 | Lee | |
| 2002/0180989 A1 | 12/2002 | Schmidt | |
| 2007/0171519 A1 | 7/2007 | Wolleschensky | |
| 2008/0218850 A1* | 9/2008 | Power | G02B 21/088 359/385 |
| 2011/0115895 A1* | 5/2011 | Huisken | G02B 21/0048 348/79 |
| 2012/0049087 A1* | 3/2012 | Choi | G01N 21/4795 250/459.1 |
| 2013/0286181 A1 | 10/2013 | Betzig et al. | |
| 2014/0099659 A1* | 4/2014 | Keller | G01N 21/6486 435/29 |
| 2014/0198200 A1 | 7/2014 | Betzig | |
| 2014/0198201 A1 | 7/2014 | Betzig | |
| 2014/0284461 A1 | 9/2014 | Betzig | |
| 2014/0285651 A1 | 9/2014 | Betzig | |
| 2014/0285653 A1 | 9/2014 | Betzig | |
| 2015/0070757 A1 | 3/2015 | Lippert et al. | |

FOREIGN PATENT DOCUMENTS

| | | |
|---|---|---|
| JP | 3938343 | 12/1939 |
| JP | 2010230 | 1/1990 |
| JP | 2239642 | 9/1990 |
| JP | 4127152 | 4/1992 |
| JP | 5324637 A | 12/1993 |
| JP | 7-253309 A | 3/1995 |
| JP | 7174687 | 7/1995 |
| JP | 8-271225 A | 10/1996 |
| JP | 8-327947 A | 12/1996 |
| JP | 2004531729 A | 10/2004 |
| WO | 02095476 A2 | 11/2002 |
| WO | WO 02095476 A3 * | 11/2003 ......... G01N 21/6458 |

OTHER PUBLICATIONS

Siedentopf, H et al. "Uber Sichtbarmachung and GroBenbestimmung ultramikroskopischer Teilchen, mit besonderer Anwendung auf Goldrubinglaser" Ann. d. Physik (4), 10, 1-39, 1903.

Steinkamp, J. et al. "Fluorescence intensity and lifetime measurement of free and particle-bound fluorophore in a sample stream by phase-sensitive flow cytometry", Review of Scientific Instruments (1999), pp. 4682-4688.

Wang, W. et al. "Optical trapping and fluorescence detection in laminar flow streams", Applied Physics Letters, American Institute of Physics (1995), pp. 1057-1059.

Cole et al., "Time-domain whole-field fluorescence lifetime imaging with optical sectioning," Journal of Microscopy, vol. 203, pt. 3, pp. 246-257 (2001).

Fuchs et al., "Thin laser light sheet microscope for microbial oceanography," Optics Express, Optical Society of America, vol. 10, No. 2, pp. 145-154 (2002).

Hell et al., "Properties of a 4pi confocal fluorescence microscope," Journal Optical Society of America, vol. 9, No. 12, pp. 2159-2166 (1992).

Huber et al., "3D light scanning macrography," Royal Microscopical Society, Journal of Microscopy, vol. 203, pp. 208-213 (2001).

Neil et al., "Wide-field optically sectioning fluorescence microscopy with laser illumination" Royal Microscopical Society, Journal of Microscopy, vol. 197, pp. 1-4 (2000).

Schaefer et al., "Structured illumination microscopy: artefact analysis and reduction utilizing a parameter optimization approach," Royal Microscopical Society, Journal of Microscopy, vol. 16, pp. 165-174 (2004).

Sharpe et al. "Optical projection tomography as a tool for 3D microscopy and gene expression studies," Science, vol. 296, pp. 541-545 (2002).

Stelzer et al., "A new tool for the observation of embryos and other large specimens: confocal theta fluorescence microscopy," Journal of Microscopy, vol. 179, pt. 1, pp. 1-10 (1995).

Voie et al., "Orthogonal-plane fluorescence optical sectioning: three-dimensional imaging of macroscopic biological specimens" Journal of Microscopy, vol. 170, pt. 3, pp. 229-236 (1993).

Voie et al., "Three-dimensional reconstructions of the cochlea from two-dimensional images of optical sections," Computerized Medical Imaging and Graphics, vol. 19, No. 5, pp. 377-384 (1995).

Voie et al., "Imaging the intact guinea pig tympanic bulla by orthogonal-plane fluorescence optical sectioning microscopy," Hearing Research, vol. 171, pp. 119-128 (2002).

Lindek et al., Confocal theta microscope with three objective lenses, Review of Scientific Instruments, vol. 65, No. 11, Nov. 1994, pp. 3367-3372.

Stelzer et al., "Fundamental reduction of the observation volume in far-field light microscopy by detection orthogonal to the illumination axis: confocal theta microscopy," Optics Communication 111,1994, pp. 536-547.

Stelzer et al., "Theory and Applications of Confocal Theta Microscopy," Proceedings on Focus on Microscopy, 95, Zoological Studies 34, Supplement 1, 1995, pp. 67-69.

* cited by examiner

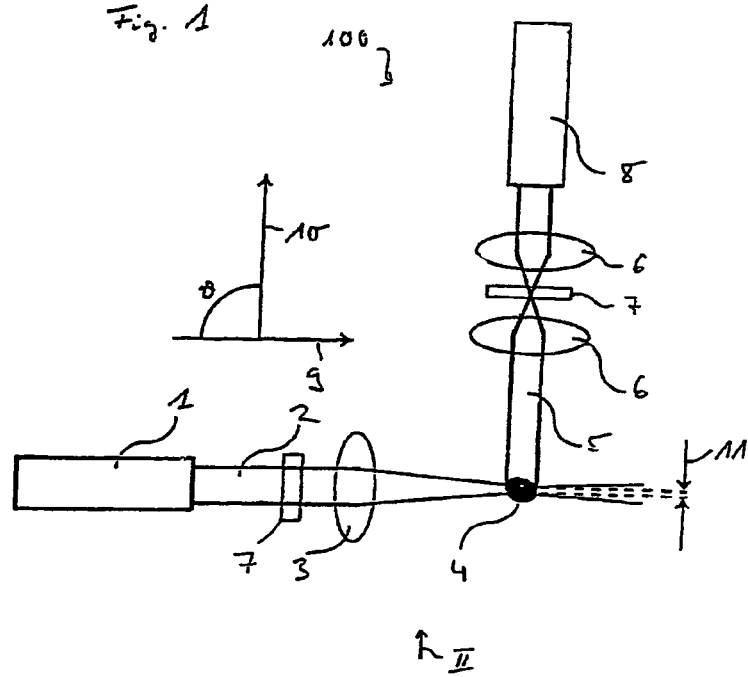
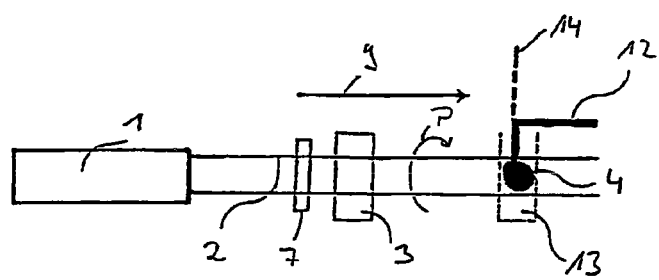

MICROSCOPE WITH A VIEWING DIRECTION PERPENDICULAR TO THE ILLUMINATION DIRECTION

The present application is a continuation of U.S. patent application Ser. No. 12/468,517 filed May 19, 2009, which is a divisional of U.S. patent application Ser. No. 10/538,081, filed Jun. 9, 2005, and claims priority to PCT/EP03/05991, filed Jun. 6, 2003 (published as WO2004/053558), which itself claims priority to German Patent Application DE 102 57 423.5, filed Dec. 9, 2002. U.S. patent application Ser. No. 10/538,081 is also a parent of co-pending continuation-in-part application U.S. patent application Ser. No. 11/592,331, filed Nov. 3, 2006.

The present invention relates to a microscope having at least one illumination beam path and at least one detection beam path, wherein the at least one illumination beam path is provided with a focusing arrangement for producing an object illumination region which extends in the direction of an illumination axis of the illumination beam path and transversely thereto, and a detection direction of the at least one detection beam path is substantially orthogonal to the object illumination region.

In contrast to work on single cells, light microscopy studies on embryos and other samples relevant to developmental biology suffer from the particular problems of absorption and resolution loss. For example, biological questions relating to gene expression patterns in developing organisms can currently be answered only with difficulty by light microscopy imaging methods, since they are often too slow, too weakly resolving or technically complex, or they do not allow millimeter-size objects to be viewed from the free working distance or from the sample holder. An acceptable solution must allow the handling of large samples and rapid high-resolution acquisition of the data, while being technically as simple as possible to implement.

The scientific literature discloses a microscope for oceanographic research, which is characterized in that it produces an illumination light plane in a sample chamber by using a laser and detects the fluorescent signals produced in the illumination light plane perpendicularly to this plane by using a camera [E. Fuchs et al., Opt. Express 10, 145 (2002)]. This microscope is similar to the ultramicroscope of H. Siedentopf and R. Zsigmondy [Ann Phys. 10(4), 1 (1903)] and is used for the detection of individual free-floating particles such as bacteria. It is not suitable for recording millimeter-size samples, for example in developmental biology, since a cuvette is used as the sample holder. It is likewise unsuitable for three-dimensional imaging, since it does not have any means of moving the sample relative to the illumination light plane.

DE 19720513 A1 or U.S. Pat. No. 5,903,781 and the scientific literature [D. Huber et al., J. Microsc. 202, 208 (2001)] disclose an instrument for three-dimensional macrography, in which an arrangement for producing light planes is used for the photographic recording of objects. In this case, an object is moved through an illumination plane and the reflected and scattered light is detected by a camera. This equipment is used to prepare three-dimensional reconstructions of centimeter-size objects. It is not, however, suitable for the use of fluorescent signals or for the high-resolution rendition of objects. A slit pattern diaphragm in conjunction with a mirror arrangement is used for producing the light planes. Owing to the use of an only linearly mobile sample stage, the sample cannot be rotated so that it is not possible to view the sample from several sides.

The technical scientific literature furthermore discloses constructions for optical tomography. Optical projection tomography is used, for example, in gene expression analysis [J. Sharpe et al., Science 296, 541 (2002)]. This is a system in which projections of biological samples are recorded, the sample being rotated about an axis perpendicular to the detection direction. Since the sample is not selectively illuminated perpendicularly to the detection axis by an illumination light plane, in contrast to the microscope according to the invention, the microscope has a very long depth of focus with which a large part of the sample can be acquired. The microscope does not therefore offer the opportunity to move the sample along the detection axis in order to record a three-dimensional image. A three-dimensional image of the sample with spatial resolution is therefore possible only by reconstruction from the projections.

DE 43 26 473 C2 discloses a confocal theta microscope, which is characterized in that it uses a first objective for point illumination and a second objective to project the object light onto a point detector, the detection direction being substantially perpendicular to the illumination direction. The confocal overlap region of the illumination volume with the detection volume is therefore particularly small, and the microscope achieves an almost isotropic resolution whose order of magnitude corresponds to the lateral resolution of a confocal microscope.

This theta microscope is arranged confocally, however, which places stringent requirements on the relative alignment of the illumination and detection focal points. Despite a large working distance, it is furthermore not readily capable of imaging large objects. This is because the object in the theta microscope does not have enough freedom of movement for scanning the object, and owing to the point detection it has to be scanned in three directions so that imaging takes a very long time. The illumination light is focused at an illumination point.

It is an object of the present invention to provide a microscope which is suitable for the high-resolution three-dimensional viewing of millimeter-size biological objects, wherein fast acquisition of the data is possible and the structure is technically as simple as possible to implement.

The present disclosure relates to a microscope having at least one illumination beam path and at least one detection beam path. The at least one illumination beam path is provided with a focusing arrangement for producing an object illumination region which extends in the direction of an illumination axis of the illumination beam path and transversely thereto. A detection direction of the at least one detection beam path is substantially orthogonal to the object illumination region and a mobile arrangement is provided for producing a relative movement between the object illumination region and an object to be studied, wherein the mobile arrangement has at least one rotational axis corresponding substantially to the direction of gravity. The sample is illuminated by a thin light strip, and the viewing takes place perpendicularly to this object illumination region, which has a two-dimensional extent. The thickness of the illumination light strip thus determines the depth of focus of the system to a substantial extent. For imaging, the object is moved through the stationary light strip, and fluorescent and/or scattered light is recorded by a two-dimensional detector in each position of the scan movement. Since the object can be rotated in the preferred embodiment, it is possible to perform such three-dimensional imaging from several sides and combine these to form a single three-dimensional image, the resolution of which is essentially determined by the lateral resolution of the individual images. The high resolution of this image results from the focused illumination, the perpendicular detection, the movement of the object and the combination of individual exposures by image processing.

The microscope according to the invention has an illumination light path and a detection light path, which preferably are mutually orthogonal in the object illumination region so that the detection direction is perpendicular to the illumination light plane. Nevertheless, the advantages of the invention are still achieved to a sufficient extent when the angle between the illumination and detection directions, or between the illumination light plane and the detection direction, does not differ too greatly from a right angle.

A laser which allows selective stimulation of fluorescent emission in the sample is preferably used as the light source. It is preferable to use a cylindrical lens for focusing the illumination light to form a thin strip, although it is also possible to use a different focusing element (for example a holographic element or a conical lens (axicon) or a phase plate or other elements for producing a Bessel beam).

The light which is detected is preferably fluorescent light. It is nevertheless also possible to detect scattered light. The detection light is preferably projected onto the detector by a telecentric system of two objectives. Other optical modules are nevertheless also suitable.

The detection is preferably carried out using a two-dimensional detector which detects the full field, for example a CCD camera. When such a detector is used, rapid imaging is possible and the movement of the sample for a three-dimensional exposure is limited to one direction (i.e. along the detection axis). The resolution of the system is determined by the lateral resolution of the detection optics.

Since the surface area of currently available detectors is generally insufficient to guarantee complete high-resolution recording of objects measuring several millimeters, in one embodiment of the microscope according to the invention it is possible to move the detector in the detection plane, i.e. essentially laterally with respect to the detection direction in order to record images of parts of the object, which can be combined to form an image of the entire object.

In a simple preferred structure, no optical elements are used for guiding the beam paths. Mirrors, dichroic mirrors, beam splitters or optical fibers, for example, may nevertheless be used for guiding the beam paths. The fact that the illumination and detection beam paths are separate in the microscope according to the invention makes it possible to obviate the use of passive components such as dichroic mirrors or active, for example acousto-optical components for separating the illumination and fluorescent light, as is customary in other fluorescence microscopes.

The structure may, for example, be supplemented with a further illumination light path, the light of which is focused to form a strip, or object illumination region, which preferably lies in the same plane as the object illumination region of the first illumination light path, so that better lighting of the sample is achieved. The light for this further illumination light path may come from the same light source. In this case, the sample is preferably illuminated from two opposite directions. The alignment workload in the microscope according to the invention is small in contrast to 4Pi confocal microscopy [S. Hell and E. H. K. Stelzer, J. Opt. Soc. Am., A 9, 2159 (1992)] since it is only necessary to superimpose two light strips which are several micrometers thick. Furthermore, the phase of the beams does not need to be taken into account.

The microscope according to the invention may nevertheless be operated as a non-confocal 4Pi theta microscope. In this case, as in a 4Pi(A) confocal microscope, the sample is illuminated coherently from two opposite directions so that an interference pattern which spatially modulates the intensity in the illumination light plane occurs along this illumination axis. The illumination volume is thereby halved, and by displacing the interference pattern (by adjusting the phase difference between the beams) it is possible to illuminate complementary regions of the sample so that an image can be reconstructed with increased resolution along the illumination axis.

The structure may be supplemented with a further detection light path, for example, by which light emitted in the opposite direction to the existing detection light path is detected. In this way, detection of the light can always take place so that the light travels as short as possible a path through the sample.

Scattered light detectors and/or transmission light detectors may additionally be provided.

Although it is possible to place the sample on a sample stage or hold it in air in the microscope according to the invention, the sample is preferably held from above by a holder in a water-filled sample chamber and can be rotated about the vertical axis, i.e. the axis in the gravitational direction. This has the advantage that there is no change in the gravity acting on the sample, and it is not deformed, when the sample is rotated for imaging from another direction. During such a rotation of the sample in the sample chamber, the sample chamber is preferably not moved so that the optical path lengths (apart from differences due to the refractive index in the sample itself) do not change during the movement process. This leads to a better image quality. The sample held in this way may advantageously be oriented so as to minimize the effect of strongly scattering or absorbing parts of the sample during the image recording.

In another embodiment of the microscope according to the invention, it is also possible to rotate the illumination and detection paths about the object to be studied while the latter is stationary. Then, however, the sample or object generally needs to be readjusted in order to be recorded in further images.

The object to be studied lies in the two-dimensional object illumination region when an image is recorded, the object being substantially larger than the thickness of this region. A two-dimensional image of the object parts located in this region is recorded by the two-dimensional detector. A three-dimensional image of the object is recorded by scanning the object in the detection direction through the stationary illumination region (or by scanning the illumination region through the object), a two-dimensional image being recorded in each position of the object. The synchronization of movement, illumination and detection is preferably optimized in order to minimize the stress on the sample.

The rotation of the object (like the linear scan movement) is preferably controlled electronically, so that the recording of a plurality of images from different angles can be automated and the speed of the sample examination can be increased. The number of images and the rotation angles of the sample which are required for recording a full image with a particular spatial resolution may be optimized in favor of a short sample examination time and therefore low stress on the sample.

Preferably, the object to be studied can also be tilted about the illumination axis so that it can also be viewed from additional directions. In another embodiment of the microscope according to the invention, a second detection light path is provided which makes it possible to detect the light emitted downward. If the object illumination region is then rotated by 90 degrees about the illumination axis (for example by rotating the cylindrical lens), then the sample can be optically sectioned horizontally (and a three-dimensional image can be produced by a vertical scan movement).

Advantageously, in the microscope according to the invention, the cylindrical lens can preferably be moved with a high frequency, for example moved in the illumination light path with a high frequency along the cylinder axis and/or the illumination axis, and/or the cylinder axis can be inclined with a high frequency in the direction of the illumination axis, so that the effect of contamination on the cylindrical lens is less strong and the sample is lit more uniformly.

Preferably, a plurality of biological samples can be held simply by being embedded in a gel (about 99% water) or another polymerizing or cros slinking structure.

The images recorded from different directions by rotating the object to be studied allow its three-dimensional reconstruction by combining the individual three-dimensional raw data records. Since only a part of the sample is imaged optimally in the preferred embodiment of the microscope according to the invention (in general the two octants which lie inside the right angle between the illumination and detection axes), at least four images are required for good reconstruction of the full sample. These images can be combined so that the reconstruction offers a higher resolution than the individual images. The quality of the reconstructed image can be improved by recording along further angles, so that the dead angles of the common optical transfer function are filled in.

When objectives with long focal lengths are used, a working distance of several millimeters is available. The size of the object is primarily limited by its optical transparency: if all of the object is intended to be studied (and not just the peripheral layers), enough light from every part of it must reach the detector in the one or other orientation.

As mentioned above, depending on the magnification of the optical system in the detection beam path, it may be necessary to displace the detector assigned to the detection beam path in order to be able to record a full image of the object to be studied, essentially owing to the limited number of detector pixels in two-dimensional pixel detectors. This means that the resolution of the overall system is essentially limited not by the numerical aperture of the optical components, in particular the lenses being used and therefore the resolution in the sample itself, but rather by the technical limitations which are encountered in the field of pixel detectors such as those used, for example, in CCD cameras. This problem may be countered by using high-resolution pixel detectors with a pixel number in the range of several millions as those used, for example, in astronomy or digital photography. These pixel detectors, however, are comparatively expensive and slow.

Another aspect of the present invention therefore relates to a microscope having at least one illumination beam path and at least one detection beam path, which is characterized in that each illumination beam path is provided with a focusing arrangement for producing a linear object illumination region which extends in the direction of an illumination axis of the illumination beam path, in that a detection direction of the at least one detection beam path is approximately orthogonal to the linear object illumination region, and in that at least one mobile arrangement is provided for producing a relative movement between the linear object illumination region and an object to be studied.

According to this aspect of the present invention, the object illumination region is therefore essentially limited to one dimension, i.e. the longitudinal dimension, so as to change over from the two-dimensional structure of the object illumination region as discussed above to an elongated or linear structure. With this linear object illumination region, accordingly, only linear sections of an object to be studied are lit and stimulated to fluoresce, or used to scatter light. These linear illuminated regions which are now produced can be imaged through the detection beam path or paths onto pixel detectors which have an elongated structure, i.e. pixels successively arranged essentially in one dimension. Such detectors, which are to be interpreted in principle as "one-dimensional" pixel detectors, can be obtained with a substantially larger pixel number, for example up to 8000 pixels. The sections of an object to be studied which are now lit by the linear object illumination region and imaged in the detector can therefore be recorded with a correspondingly high resolution actually in the detector itself, and correspondingly converted into high-resolution images. Since the dimension of the pixels present in such pixel detectors, transversely to the longitudinal extent of the pixel detector, is generally much smaller than the width of the image of the linear object illumination region in this direction, even when taking into account the magnification produced in the detection beam path, it may be preferable to change over to elongated "two-dimensional" pixel detectors which, for example, have a pixel number of 64×4096, i.e. a substantially larger pixel number in the longitudinal direction of the object illumination region, or the corresponding image thereof, than transversely thereto.

In order then to be able to fully image an object to be studied with such a system, or to be able to produce a complete image of it, scanning may be carried out between the object to be studied and the illumination beam path or the detection beam path so that, in principle, the object to be studied is linearly sampled and the individual line images thereby produced can then be combined to form a full image.

In order to facilitate this, for example, the at least one mobile arrangement may be designed to produce a relative movement between the object and the linear object illumination region essentially orthogonally to the illumination axis and the detection direction. To this end, for example, the at least one mobile arrangement may be designed to move the object so as to produce a relative movement.

Alternatively or in addition to this displacement of the object to be studied, the at least one mobile arrangement may be designed to move the at least one illumination beam path at least in the linear object illumination region provided by it, in order to produce the relative movement. Since the object illumination region is in this case shifted while the object is stationary, for example, it is then necessary for the at least one mobile arrangement to be designed to move the at least one detection beam path in accordance with the movement of the at least one illumination beam path, at least in its region near the object.

As mentioned above, the at least one detection beam path may have a detector with a multiplicity of detector pixels, in which case it may be preferable to select the number and positioning of the detector pixels of the detector so that the at least one detection beam path projects a section of the object, illuminated by the at least one illumination beam path in the object illumination region, essentially fully onto the detector.

In order to be able to produce not only a surface image of an object to be studied with the system according to the invention, but also to be able to image it three-dimensionally by three-dimensional sampling, it is furthermore proposed for the at least one mobile arrangement to be designed to move the object to be studied, essentially in the direction of the detection direction of the at least one detection beam path.

From the explanations above, it is clear that an essential principle of the present invention is to produce an elongated object illumination region with at least one illumination beam path, in which an object to be studied can then be positioned in order to produce an image of the section of the object to be studied positioned in the object illumination region, or optionally the entire object, by stimulating fluorescence or by generating scattered light in at least one detection beam path.

The present invention therefore also relates to a microscope which has at least one illumination beam path and at least one detection beam path, and is characterized in that each illumination beam path is provided with a focusing arrangement for producing an object illumination region which extends in the direction of an illumination axis of the illumination beam path, in that a detection device of the at least one detection beam path is approximately orthogonal to the object illumination region, and in that a mobile arrangement is provided for producing a relative movement between the object illumination region and an object to be studied.

The invention will be explained in more detail below with reference to the appended drawings, in which:

FIG. 1 shows the schematic representation of the beam path in one embodiment of the microscope according to the invention, a single illumination beam path and a single detection beam path being provided, seen in observation direction I of FIG. 2;

FIG. 2 shows the embodiment represented in FIG. 1 in observation direction II in FIG. 1;

Figure 3:
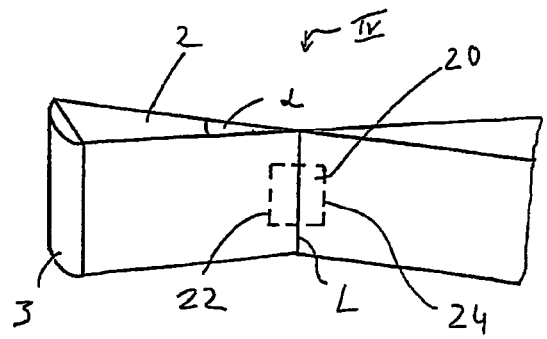
FIG. 3 shows an outline representation of the illumination beam path, which emerges from a cylindrical lens and forms an object illumination region in the region of a focus line.

FIG. 1 shows an embodiment of a microscope 100 according to the invention. The structure comprises a light source 1, the collimated light beam 2 from which is focused into the sample 4 by a cylindrical lens 3. This creates a thin vertical light strip 11 by which fluorescent emission can be induced in the sample 4. The emitted light 5 is projected through detection optics 6 onto the two-dimensional detector 8, for example a CCD camera.

The structure is particularly simple owing to the right-angled arrangement (=90 degrees) of the illumination direction 9 and the detection direction 10. In particular, the use of dichroic mirrors for separating the illumination and fluorescent light in the detection beam path 5 can be obviated. The filters 7 in the illumination beam path 2 and in the detection beam path 5 are glass filters or acousto-/electro-/magneto-optical filters, and allow selective choice of wavelengths for the illumination and the detection.

The sample 4 is held in a sample chamber 13 by a holder 12, and is moved through the stationary light plane 11 in the detection direction 10 for imaging. The holder 12 also makes it possible to rotate the sample 4 about its vertical axis 14, so that the sample 4 can be illuminated and viewed from several sides.

Figure 4:
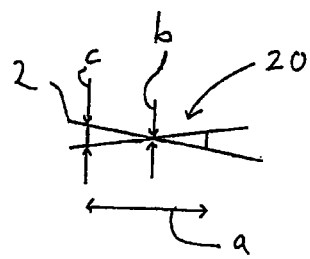
FIG. 4 shows a plan view of the beam path of FIG. 3 in observation direction IV in FIG. 3.

FIGS. 3 and 4 show in outline the aforementioned illumination beam path 2 which is produced with the aid of the cylindrical lens 3. Using the cylindrical lens 3, whose focal length may preferably lie in the range of from 10 mm to 100 mm, light emitted by the light source 1 is focused at a comparatively small angle α. In the region of a focus line L, this creates an object illumination region 20 indicated by dashes in FIG. 3, which approximately has a two-dimensional or flat structure or extent, and is formed by cylinder sections on either side of the focus line. With a dimension a of about 5 mm for this object illumination region 20 as measured in the direction of the illumination axis, or illumination direction, and with a thickness dimension of about 20 μm for the illumination beam path 2 in the region of the focus line b, a thickness dimension c of approximately 60 μm is obtained at the end regions 22, 24 of the object illumination region 20 lying in the illumination direction, although this naturally depends on the numerical aperture provided for the cylindrical lens 3. Throughout the object illumination region 20, there is therefore a negligible variation—expressed in terms of the dimensions of the objects to be studied—in the thickness of the object illumination region 20 in the illumination beam path 2, so that, in particular taking into account the dimensions of the objects to be studied, a constant thickness of the object illumination region and therefore a two-dimensional or planar structure thereof can be assumed here to a first approximation.

Figure 5:
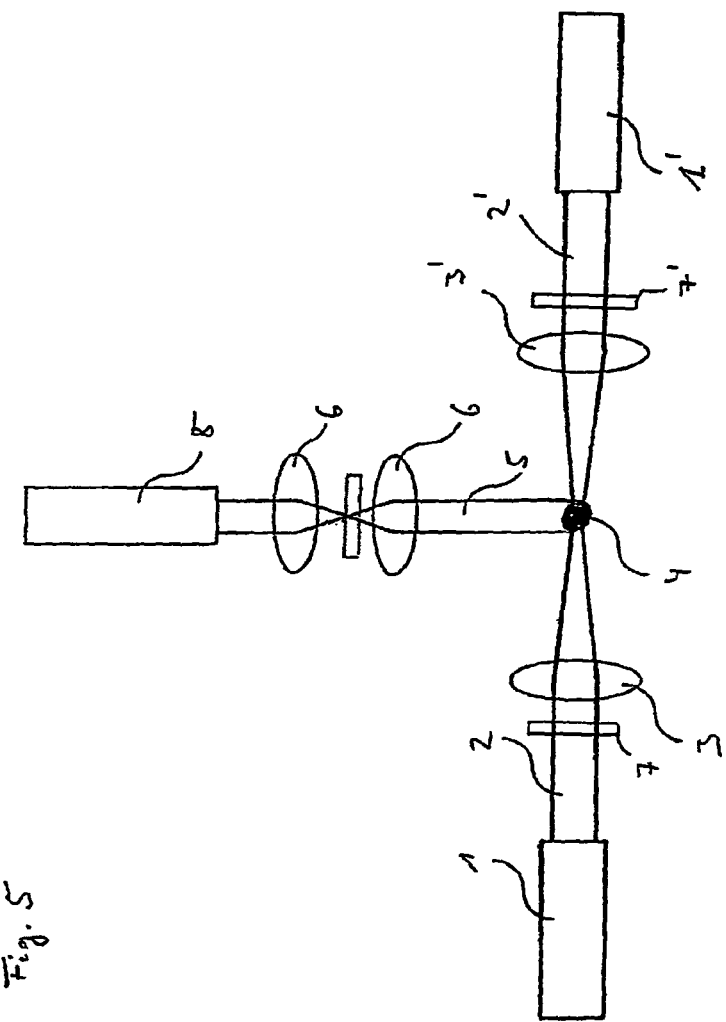
FIG. 5 shows the schematic representation of the beam path in another embodiment of the microscope according to the invention, two illumination beam paths being provided.

FIG. 5 represents a modified configuration of the microscope 100, in which two illumination beam paths 2, 2' are provided. In the case represented, each of these two illumination beam paths 2, 2', which have oppositely directed illumination directions but illumination axes corresponding to each other, respectively has a cylindrical lens 3, 3' with optionally assigned filters 7, 7' and a light source 1, 1'. In a variant of this configuration, it is furthermore possible to provide more than just one light source. By superposition of the two object illumination regions of these illumination beam paths 2, 2', which object illumination regions were presented in more detail above with reference to FIGS. 3 and 4, this creates a thin vertical light strip which is more homogeneous compared to the light strip in the embodiment represented in FIG. 1. The emitted light 5 is projected through detection optics 6 onto the two-dimensional detector 8. This embodiment of the microscope according to the invention is particularly suitable for absorbent samples, for which it is not possible to illuminate the entire sample with illumination from one side.

In this configuration, it is possible to make the two illumination beam paths 2, 2', or their light beams, interfere deliberately by defined adjustment of the phase angle of these light beams with respect to each other, wherever the two object illumination regions of these two illumination beam paths 2, 2' mutually overlap. In this way, in the region where the object or sample 4 to be studied is to be illuminated, it is possible to stop out particular sections by destructive interference or highlight particular regions by constructive interference, so that the resolution of the overall system can be further improved.

Figure 6:
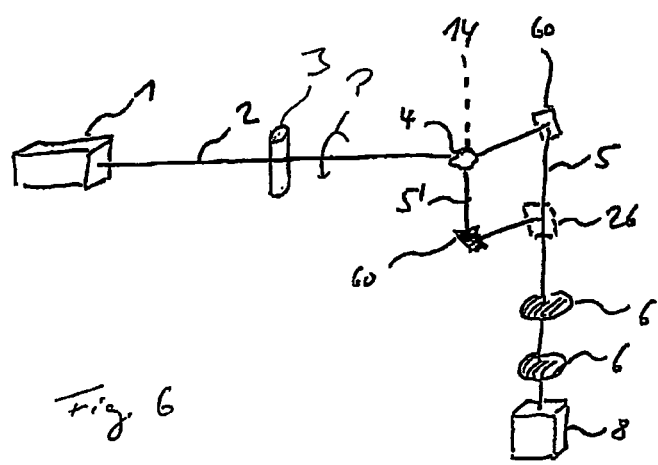
FIG. 6 shows another outline representation of a microscope according to the invention.

FIG. 6 depicts another variant of the microscope 100 according to the invention. The arrow P indicates that the cylindrical lens 3 shown therein can be rotated, for example through 90°, about the illumination axis of the illumination beam path 2. The object illumination region 20 of this illumination beam path 2 is thereby also rotated so that, starting from the orientation shown in FIG. 2 in which it lies essentially in the plane of the drawing, it is rotated through 90° and is then perpendicular to the plane of the drawing. In this way, it is possible to view the object 4 to be studied from a different direction, i.e. the direction lying below this object 4 in the representation of FIG. 2. It is also possible to provide a further detection beam path 5' with which, in relation to the detection beam path 5 visible in FIG. 1, the object 4 to be studied can be viewed at an angle of 90° without this object 4 itself having been rotated.

In such a system, for example by using mirrors 60 and a tilting mirror 26, it is possible to guide different detection beam paths 5, 5' selectively to the same detector 8, or the same optical system with objectives 6, according to the position of the tilting mirror 26. In accordance with the rotational position of the cylindrical lens 3, the tilting mirror 26 will then correspondingly be switched over. It is of course possible to provide two detection beam paths 5, 5' with a respectively assigned objective arrangement and detector, independently of each other and for example at an angle of 90°. It is also possible to make at least one of these systems mobile such that it can be rotated together with the cylindrical lens 3 about the illumination axis of the illumination beam path 2 in FIG. 2, so that imaging can then be produced all around the object 4 to be studied by simultaneously rotating the cylindrical lens 3 and this detection beam path, without this object itself having been moved.

Figure 7:
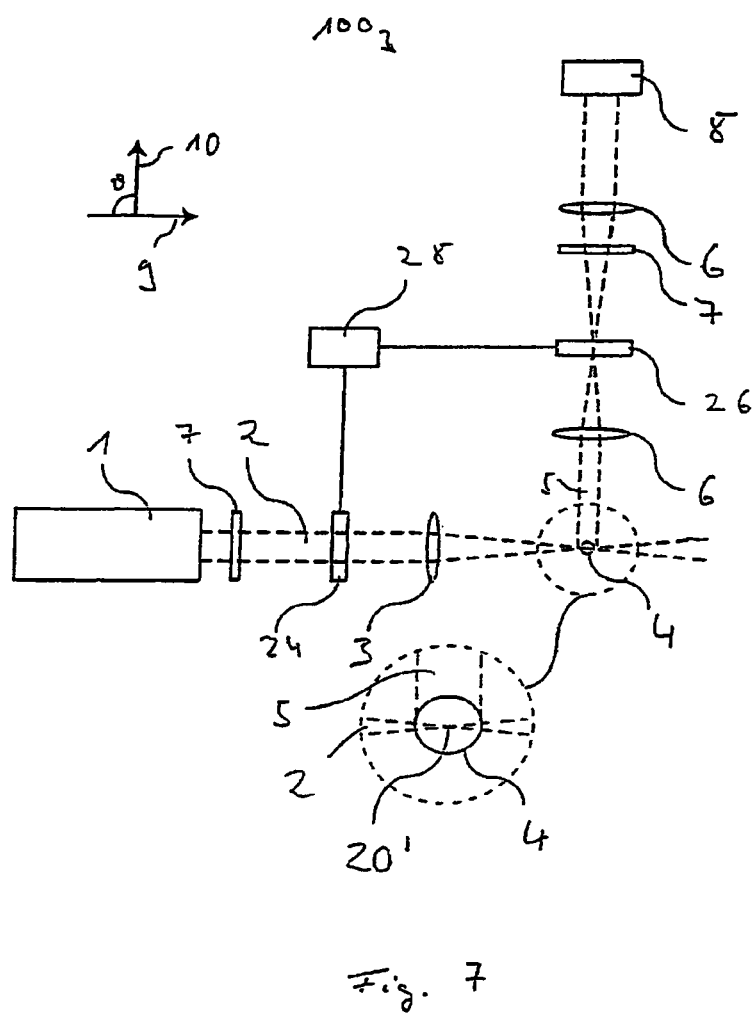
FIG. 7 shows a view corresponding to FIG. 1 of an alternatively configured microscope according to the invention.

An alternatively configured microscope 100 according to the invention is represented in FIG. 7. The basic structure, as well as the viewing mode, are the same as in FIG. 1 so that reference may generally be made to the comments above. There is again an illumination beam path, essentially provided by the light beam 2, which is focused by using an optical system in order to generate an object illumination region 20'. The lens 3 used here is no longer a cylindrical lens, but a lens which is rotationally symmetric with respect to the illumination axis 9 of the illumination beam path. This generates an object illumination region 20' which is likewise essentially rotationally symmetric and therefore, particularly in the region where the object 4 to be studied i.e. the sample is positioned, can be interpreted as a linear object illumination region or line-like object illumination region. The dimensions of this essentially rotationally symmetric linear object illumination region may, naturally depending on the focal length of the lens 3 or of the optical system being used, be in the range of 10-20 μm at the center while having a dimension in the range of 40-60 μm in the edge regions.

In this microscope 100 as shown in FIG. 7, therefore, a correspondingly linear region instead of a wafer-like or two-dimensional region of the sample 4 is lit when a sample 4 is positioned in the object illumination region 20'. The image of this linearly illuminated region as produced in the detection beam path 5 is projected via its optical system onto the detector 8, so that an optionally magnified line image is generated there. The detector 8 is constructed as a pixel detector and, in accordance with the linear image now produced, has more of a "one-dimensional" pixel arrangement. In this arrangement, the positioning of the pixels is such that a substantially larger number of the pixels will lie successively in the longitudinal direction of the linear image which is produced, than transversely thereto. The number of pixels in the longitudinal direction or transverse direction is preferably selected so that the linear image produced in the detection beam path 5 can be recorded fully by the detector 8 without having to move the latter. In the extreme case, it is even possible to provide a single row of pixels. Here, it should be borne in mind that with a decreasing width of such a pixel array and progressive transition to a single pixel line, the number of pixels present in such a linear arrangement can be increased and hence the resolution of the detector 8 can be enhanced correspondingly in this direction.

In order to be able to produce full images of the sample 4 with this high-resolution microscope 100 as represented in FIG. 7, even in view of the possible structure of the detector 8, a relative movement of this sample 4 with respect to the linear object illumination region 20' is produced according to the invention. There are in principle various ways of doing this. On the one hand, the sample 4 may be displaced orthogonally to the linear object illumination region and also orthogonally to the detection beam path 5, i.e. perpendicularly to the plane of the drawing in the representation of FIG. 7. In this way, linear regions of the sample 4 are successively illuminated by scanning, so that a full image of the sample 4 in a plane can be produced by combining the correspondingly recorded images. In order to generate a three-dimensional image, the sample may furthermore be displaced in the direction of the detection beam path 5 or the detection direction 10, so that various planes of the sample 4 are moved through the focal plane of the illumination beam path 5.

In an alternative variant represented in FIG. 7, the sample 4 may be kept stationary while providing devices 24 and 26 both in the illumination beam path 2 and in the detection beam path 5 which facilitate displacement of these two beam paths 2, 5 in their region near the sample. For example, these devices 24, 26 may be beam deflection units which, for example, respectively contain a tiltable mirror. The two beam deflection units 24, 26 are operated by a control device 28 in order to match their movements to each other, which ensures that the region of the sample 4 currently being lit by the object illumination region 20' is always projected through the detection beam path 5 onto the detector 8. In this way it is possible for the sample, which otherwise cannot be moved perpendicularly to the plane of the drawing in FIG. 7, to be scanned in a plane. Here again, in order to obtain a three-dimensional representation, the sample 4 is then displaced again in the detection direction 10 in order to sample a plurality of planes in succession.

It is of course also possible to combine the two aforementioned ways of producing a relative movement between the sample 4, on the one hand, and the beam paths, on the other hand, in which case it should be borne in mind that the movement of the beam paths can be carried out faster than the movement of the sample.

With the system as represented in FIG. 7, it is thus possible to use high-resolution "one-dimensional" or elongated pixel arrays in the detector 8 in order to be able to produce correspondingly high-resolution images of the respectively lit regions of the sample 4. A further advantage of this "sampling" of the sample 4 is that the position of the object illumination region can be matched better to the field of view of the detection optics, i.e. regions which are not intended to be imaged do not have to be sampled or illuminated at all, without causing any deterioration of the sampling or imaging of other regions of interest. This scan movement of the linear object illumination region with respect to the sample to be studied furthermore gradually generates an illumination plane or a two-dimensional object illumination region which has a more homogeneous intensity in the direction of the relative movement than is the case with corresponding beam expansion in the systems described above, since the intensity profile in the object illumination region therein is also dependent on the intensity profile of the focused light beam. Higher intensities can also be achieved owing to the stronger focusing of the light. The laser power is therefore used more efficiently, which is advantageous particularly for weak fluorescence or multi-photon stimulation.

It should be pointed out that various aspects of the microscope according to the invention, for example the provision of different numbers of illumination beam paths and detection beam paths, or the relative positioning and phase adjustment thereof, the measures for moving an object by displacement or rotation or for moving the optical system, for example while the object is stationary, may of course be implemented irrespective of whether the object illumination region has a two-dimensional extent or is formed essentially as a band or linearly.

The invention relates to a microscope in which a layer of the sample is illuminated by a thin light strip 11 and the viewing takes place perpendicularly to the plane of the light strip. The thickness of the light strip 11 therefore essentially determines the depth of focus of the system. For the imaging, the object 4 is moved through the light strip 11 which is stationary with respect to the detector, and fluorescent and/or scattered light is recorded by a two-dimensional detector. Strongly absorbing or strongly scattering objects 4 are viewed from several spatial directions. The three-dimensional images which are recorded from each direction can subsequently be combined to form an image in which the data are weighted according to their resolution. The resolution of the combined image will then be dominated by the lateral resolution of the individual images.

The invention claimed is:

1. A microscope having at least one illumination beam path and at least one detection beam path, wherein
   the at least one illumination beam path is provided with a focusing arrangement for producing an object illumination region which extends in a direction of an illumination axis of the illumination beam path and transversely thereto,
   a detection direction of the at least one detection beam path is substantially orthogonal to the object illumination region, and
   a mobile arrangement is provided for producing a relative movement between the object illumination region and an object to be studied, wherein, for illumination from different directions, the object is rotatable about a vertical axis of the mobile arrangement corresponding substantially to a vertical direction along a direction of gravity, and wherein the relative movement comprises at least one of a translation of the object or a displacement of the illumination beam path and the detection beam path, and wherein the object illumination region is a substantially two-dimensional light stripe which extends in the direction of the illumination axis of the illumination beam path and transversely thereto in the vertical direction.

2. The microscope as claimed in claim 1, wherein the object is moveable by the mobile arrangement while the object illumination region is substantially stationary.

3. The microscope as claimed in claim 1, wherein the object illumination region is moveable by the mobile arrangement while the object is substantially stationary.

4. The microscope as claimed in claim 1, wherein a cylindrical lens is arranged in the at least one illumination beam path for focusing the illumination light.

5. The microscope as claimed in claim 4, wherein the cylindrical lens is moveable by at least one of a rotational movement about the illumination axis or a displacement movement in at least one of the direction of the illumination axis or a direction of a cylinder axis of the cylindrical lens, or is capable of being tilted via the cylinder axis with respect to the illumination axis.

6. The microscope as claimed in claim 5, wherein the cylindrical lens is moveable by a high-frequency movement.

7. The microscope as claimed in claim 1, wherein scattered light or fluorescent light of one or more wavelengths is used.

8. The microscope as claimed in claim 1, wherein the illumination light beam is produced by a light source producing light of one or more wavelengths.

9. The microscope as claimed in claim 1, wherein the mobile arrangement comprises a holder for holding the object in a sample chamber in which the object is moved about the at least one rotational axis corresponding substantially to the direction of gravity.

10. The microscope as claimed in claim 1, further comprising at least two illumination beam paths with substantially opposite illumination directions for producing at least locally overlapping object illumination regions.

11. The microscope as claimed in claim 10, wherein illumination light of the at least two illumination beam paths interferes at least locally along said substantially opposite illumination directions substantially in the object illumination region.

12. The microscope as claimed in claim 11, wherein the illumination light of the two illumination beam paths has a constant, adjustable phase.

13. The microscope as claimed in claim 1, wherein a detector is arranged at the at least one detection beam path, and wherein the detector is laterally moveable with respect to the detection direction of the at least one detection beam path.

14. The microscope as claimed in claim 1, wherein the at least one detection beam path is capable of being adapted such that the detection direction is approximately orthogonal to the object illumination region when the object illumination region is shifted.

15. The microscope as claimed in claim 1, wherein the object illumination region is substantially planar-shaped.

16. The microscope as claimed in claim 1, wherein the object illumination region is substantially linearly-shaped.

17. The microscope as claimed in claim 1, wherein the at least one rotational axis is substantially perpendicular to said illumination axis and substantially perpendicular to said detection direction.

18. A microscope having at least one illumination beam path and at least one detection beam path, wherein
   the at least one illumination beam path is provided with a focusing arrangement for producing an object illumination region which extends in a direction of an illumination axis of the illumination beam path and transversely thereto,
   a detection direction of the at least one detection beam path is substantially orthogonal to the object illumination region,
   a mobile arrangement is provided for producing a relative movement between the object illumination region and an object to be studied,
   such that the mobile arrangement produces, for illumination from different directions, a rotational movement of the object and at least one of a translation of the object or a displacement of the illumination beam path and the detection beam path, wherein the rotational movement has a vertical rotational axis corresponding substantially to a vertical direction along a direction of gravity, wherein the rotational axis is substantially orthogonal to the illumination axis and substantially orthogonal to the detection direction, wherein the object illumination region is a substantially two-dimensional light stripe which extends in the direction of the illumination axis of the illumination beam path and transversely thereto in the vertical direction.

19. The microscope as claimed in claim 18, wherein the object is moveable by the mobile arrangement while the object illumination region is substantially stationary.

20. The microscope as claimed in claim 18, wherein the object illumination region is moveable by the mobile arrangement while the object is substantially stationary.

21. The microscope as claimed in claim 18, wherein a cylindrical lens is arranged in the at least one illumination beam path for focusing the illumination light.

22. The microscope as claimed in claim 21, wherein the cylindrical lens is moveable by at least one of a rotational movement about the illumination axis or a displacement movement in at least one of the direction of the illumination axis or a direction of a cylinder axis of the cylindrical lens, or capable of being tilted via the cylinder axis with respect to the illumination axis.

23. The microscope as claimed in claim 22, the cylindrical lens is moveable by a high-frequency movement.

24. The microscope as claimed in claim 18, wherein scattered light or fluorescent light of one or more wavelengths is used.

25. The microscope as claimed in claim 18, wherein the illumination light beam is produced by a light source producing light of one or more wavelengths.

26. The microscope as claimed in claim 18, comprising at least two illumination beam paths with substantially opposite illumination directions for producing at least locally overlapping object illumination regions.

27. The microscope as claimed in claim 26, wherein illumination light of the at least two illumination beam paths interferes at least locally along said substantially opposite illumination directions substantially in the object illumination region.

28. The microscope as claimed in claim 27, wherein the illumination light of the two illumination beam paths has a constant, adjustable phase.

29. The microscope as claimed in claim 18, wherein a detector is arranged at the at least one detection beam path, and wherein the detector is laterally moveable with respect to the detection direction of the at least one detection beam path.

30. The microscope as claimed in claim 18, wherein the at least one detection beam path is capable of being adapted such that the detection direction is approximately orthogonal to the object illumination region when the object illumination region is shifted.

31. The microscope as claimed in claim 18, wherein the object illumination region is substantially planar-shaped.

32. The microscope as claimed in claim 18, wherein the object illumination region is substantially linearly-shaped.

33. The microscope as claimed in claim 18, wherein the mobile arrangement provides at least one rotational axis being substantially perpendicular to said illumination axis and substantially perpendicular to said detection direction.

34. A microscope having at least one illumination beam path and at least one detection beam path, wherein
the at least one illumination beam path is provided with a focusing arrangement for producing an object illumination region which extends in a direction of an illumination axis of the illumination beam path and transversely thereto,
a detection direction of the at least one detection beam path is substantially orthogonal to the object illumination region,
a mobile arrangement is provided for producing a relative movement between the object illumination region and an object to be studied, and
wherein the object is mounted on a holder, the holder being movable within a sample chamber, such that the mobile arrangement produces, for illumination from different directions, a rotational movement and at least one of a translational movement of the object within the sample chamber or a displacement of the illumination beam path and the detection beam path, wherein the rotational movement has a vertical rotational axis corresponding substantially to a vertical direction along a direction of gravity, and wherein the object illumination region is a substantially two-dimensional and vertically oriented light stripe which extends in the direction of the illumination axis of the illumination beam path and transversely thereto in the vertical direction.

* * * * *